United States Patent [19]
Jones

[11] 3,932,417
[45] Jan. 13, 1976

[54] DIMERIC INDOLE ALKALOID PURIFICATION PROCESS
[75] Inventor: William E. Jones, Indianapolis, Ind.
[73] Assignee: Eli Lilly and Company, Indianapolis, Ind.
[22] Filed: Oct. 24, 1973
[21] Appl. No.: 409,225

[52] U.S. Cl. .......................................... 260/287 R
[51] Int. Cl.² ...................................... C07D 215/00
[58] Field of Search ...................... 260/287 R, 287 P

[56] References Cited
UNITED STATES PATENTS

| | | | |
|---|---|---|---|
| 3,097,137 | 7/1963 | Beer et al. | 260/287 R |
| 3,205,220 | 9/1965 | Svoboda et al. | 260/287 R |
| 3,225,030 | 12/1965 | Svoboda | 260/287 R |

OTHER PUBLICATIONS
Stahl et al., *Chemical Abstracts*, 1971, Vol. 75, abst. 29733a.

*Primary Examiner*—Nicholas S. Rizzo
*Assistant Examiner*—David E. Wheeler
*Attorney, Agent, or Firm*—James L. Rowe; Everet F. Smith

[57] ABSTRACT

Dimeric indole alkolids-vinblastine, des-N-methyl-vinblastine and vincristine-are purified by extracting leaves of *Vinca rosea* with acid, neutralizing the acidic solution, extracting the dimeric alkaloids into an aromatic solvent, optionally subjecting the extracted alkaloids to gel exclusion chromatography, precipitating the dimeric alkaloids as sulfate salts and finally separating the dimeric alkaloids by high-pressure chromatography.

2 Claims, No Drawings

DIMERIC INDOLE ALKALOID PURIFICATION PROCESS

BACKGROUND OF THE INVENTION

Vinblastine (vincaleucoblastine or VLB) was isolated by Beer et al., U.S. Pat. No. 3,097,137, by extraction of *Vinca rosea* leaves with ethanol and acetic acid, acidification of the extract with hydrochloric acid, extraction of the acidic aqueous solution with benzene followed by pH gradient elution chromatography of the benzene-extracted alkaloids over alumina. An improved process for preparing vinblastine and its companion alkaloid, leurosine, is contained in Svoboda, U.S. Pat. No. 3,225,030. According to the process of this patent, the leaves of *Vinca rosea* are extracted into a tartaric acid-benzene solvent system, the benzene layer is neutralized, the base-insoluble alkaloids are extracted into benzene, and the benzene extract is then subjected to a chromatographic separation procedure in which leurosine and vinblastine are successively eluted. The separation of vincristine (leurocristine) from other dimeric Vinca alkaloids is described in Svoboda et al., U.S. Pat. No. 3,205,220. Here again *Vinca rosea* leaves are extracted with a mixture of benzene and tartaric acid. The mother liquors eventually obtained after crystallization of vinblastine sulfate by either of the procedures of the above two patents are subjected to a citric acid extraction procedure first at pH = 4.4 and then at pH = 7.0. The alkaloids obtained by evaporation of the benzene eluant at this higher pH are chromatographed over deactivated alumina, and vincristine is eluted after vinrosidine (leurosidine).

More recently, West German Pat. No. 2,124,023 describes a process for purifying the three principle dimeric anti-cancer alkaloids of *Vinca rosea*: vinblastine, vincristine and leurosine. According to the process of this patent, vinca leaves are extracted with aqueous methanol and the dimeric alkaloids thus extracted are converted to acid addition salts in solution, preferably sulfates. The acidic extract is then extracted with benzene, the benzene extracts being discarded. The acidic layer is next made alkaline and the alkaloids extracted into benzene. This benzene extract is evaporated to dryness and the residual alkaloids again converted to the corresponding sulfate salts with 10 percent sulfuric acid. A mixture of the crystalline sulfates of the 3-dimeric alkaloids is obtained, and these are separated by chromatography using methylenechloride and chloroform as the elution solvents. Alternatively, the alkaloidal bases are separated by chromatography without first converting them to sulfate salts.

Finally, Hungarian Pat. No. 154,715 published 11-2-2-67 describes a process in which vinca leaves are treated with ammonium hydroxide, and then with toluene. The toluene extract is contacted with hydrochloric acid, and the remaining alkaloid mixture extracted with ethylenedichloride at pH =9. This alkaloid fraction is then chromatographed over neutral alumina. The vinblastine and leurosine fractions are eluted with benzene-ether. (No mention is made of the isolation of vincristine in this particular patent). The methanol extraction procedure outlined in West German Pat. No. 2,124,023 is also disclosed in the aforesaid Hungarian patent.

It is an object of this invention to provide a process for the purification of vincristine, des-N-methylvinblastine and vinblastine starting with *Vinca rosea* leaves, which process yields the desired dimeric alkaloids in greater quantity and with a higher degree of purity than any of the previously described processes.

SUMMARY OF THE INVENTION

In the fulfillment of the above and other objects, this invention provides a process for the purification of dimeric indole alkaloids which comprises extraction of *Vinca rosea* leaves or other natural source of dimeric alkaloids with aqueous acid (pH = 3), extraction of the aqueous extract with a water-immiscible solvent, adjustment of the pH of the aqueous extract to 6, extraction of the acidic aqueous layer with a water-immiscible solvent, the acidic layer being discarded, and evaporation of the extraction solvent to yield residual alkaloids. At this point, an optional purification step, comprising gel exclusion chromatography of the alkaloids using a citrate buffer system at pH = 7, can be employed followed by extraction of the dimeric alkaloids from aqueous citrate with a water-immiscible solvent to yield alkaloidal bases. Whether or not the gel filtration step is employed, the next step in the process involves precipitation of the residual dimeric alkaloids as sulfate salts from ethanol or other suitable solvent followed by chromatographic (preferably high pressure) purification of the dimeric alkaloids either as free bases or as sulfate salts.

In carrying out the above process, the leaves of plants containing crude vinca alkaloids such as *Catharanthus roseus* (*Vinca rosea*) are extracted at pH $\simeq$ 3 using sulfuric acid to maintain the desired acidity. The water immiscible solvent commonly used to extract the aqueous acidic layer is benzene, although other water-immiscible organic solvents such as toluene and the like can be used. After the pH of the aqueous acidic extract has been adjusted to about 6 by the addition of sodium hydroxide, ammonium hydroxide or other base, the dimeric alkaloids are extracted into an organic solvent. The re-extraction solvent is customarily benzene although, again, other water-immiscible organic solvents can be employed. The optional gel exclusion chromatography step is carried out using a cross-linked dextran gel (sephadex G-25 F) in a citrate buffer system. The mobile phase is a pH = 3.0, 0.1M ammonium citrate buffer although, as will be apparent to those skilled in the art, other buffer systems at pH = 3 can be used interchangeably with citrate buffer in the gel exclusion chromatography system. A pressure of about 15 psi is employed during gel-exclusion chromatography. In this process, the dimeric alkaloid fraction containing vincristine, vinblastine, des-N-methylvinblastine, leurosine and vinrosidine is eluted first. The dimeric alkaloids are extracted from the pH = 3 buffer by adjusting the pH of the aqueous solution to pH = 7.0 with ammonium hydroxide and then contacting the aqueous pH = 7 solution with a water-immiscible solvent, preferably again benzene. Evaporation of the benzene yields a residue which can be dissolved in ethanol and leurosine crystallized directly therefrom. The leurosine is separated by decantation, and the supernate thus obtained is acidified to pH = 4.2 with 3 percent ethanolic sulfuric acid to convert the remaining dimeric alkaloids to their sulfate salts. The mixed sulfate salts precipitate, are collected and are converted to the corresponding free alkaloidal bases by standard procedures as, for example, by dissolving the salts in water, adjusting the pH $\simeq$ 8.0 with ammonium hydroxide and extracting the dimeric alkaloids with a water-immiscible organic solvent, preferably at this point in the procedure, methylenedichloride. Evaporation of the methylenedichloride yields the mixed dimeric alkaloids which are then chromatographed at high pressure over alumina (Activity III) using a methyl acetate-methylenedichloride-water (48:51:1) solvent system as the eluant.

Operating pressures employed have been in the range 150–350 psi. As will be understood by those skilled in the art of high-pressure chromatography, equipment is available to carry out procedures at 4000–5000 psi and pressures in the range 7500–8000 psi appear feasible. Alkaloidal separation is in general more efficient at the higher pressures. High-pressure chromatography procedures are carried out in stainless steel equipment equipped with pressure resistant fittings.

The alkaloids are eluted in the following order from this chromatographic procedure: leurosine, vinblastine, des-N-methylvinblastine, vincristine and vinrosidine. Identification of the dimeric alkaloid in the eluant fraction is carried out by standard procedures known to the art, as by thin layer chromatography. Collection of fractions containing vinblastine, des-N-methylvinblastine or vincristine followed by evaporation of the solvents in vacuo and conversion of the vinblastine, des-N-methyl-vinblastine or vincristine to the corresponding sulfate salt at pH = 4.2 with ethanolic sulfuric acid completes the separation and purification procedure. Specific examples of the process of this invention follow:

EXAMPLE 1

Vincristine Purification

Ten kilograms of dry *Catharanthus roseus* leaf were extracted three times for one-hour periods, using 32 volumes of 50°C. water acidified to pH = 3.0 by the addition of 30 percent (w/v) sulfuric acid as the extracting medium. The aqueous extracts were decanted from fibrous material, combined and filtered. The filtrate was extracted twice with equal volumes of benzene, and the benzene extracts discarded. The pH of the filtrate was then raised to pH = 6.0 by the addition of concentrated ammonium hydroxide. The aqueous phase at pH = 6.0 was extracted three times with equal volumes of benzene. The benzene extracts were combined and concentrated in vacuo to yield as a residue 57 g. of a crude alkaloid mixture (VRA).

5 g. of VRA thus obtained were dissolved in 250 ml. of pH = 3.0, 0.1M ammonium citrate buffer and the resulting filtrate was chromatographed over 600 g. of a crosslinked dextran gel (sephadex G-25 F) in a 5 × 140 cm. glass column. 0.1 M ammonium citrate buffer (pH = 3.0) was used as the mobile phase. The column was developed under a head pressure of 15 psi, giving an effluent flow rate in the range 10–14 ml. per minute. Fractions were collected and identified as containing predominantly monomeric or dimeric alkaloids by thin layer chromatography. Those fractions containing the dimeric alkaloids were eluted first and included, by thin-layer chromatography, vinblastine, vincristine, leurosine and vinrosidine. The aqueous fractions containing predominantly these dimeric alkaloids were combined, the pH adjusted to 7.0 with ammonium hydroxide, and the resulting neutral aqueous solution extracted three times with one-half its volume of benzene. The benzene extracts were combined and filtered through anhydrous sodium sulfate. Concentration of the filtrate to dryness in vacuo yielded 1.0 g. of dimeric alkaloid mixture. The mixture was dissolved in 7.5 volumes of anhydrous ethanol. Leurosine crystallized at this point and was separated by centrifugation; yield = 157 mg. of leurosine. The supernate was adjusted to pH = 4.2 with 3 percent ethanolic sulfuric acid. Sulfates of the remaining dimeric alkaloids formed immediately as needles, and crystallization was allowed to continue for two days. The crystals were separated by centrifugation, washed with ethanol and dried. A yield of 241 mg of mixed sulfate salts of vinblastine and vincristine, plus a small quantity of leurosine sulfate were obtained. The salts were converted to the corresponding free bases by dissolving the salts in water, adjusting the pH of the aqueous solution to 8.0 with 14 N ammonium hydroxide and then extracting the water-insoluble bases into methylenechloride. The methylenechloride extract was filtered, and the solvent removed by evaporation in vacuo. The resulting residue was chromatographed over 400 g. of alumina (Activity III, 200 m$^2$/g) using a methyl acetate-methylenechloride-water (48:51:1) solvent system as the eluant. Chromatography was carried out in a stainless steel column, 8 mm by 7 m, at a pressure of 250–325 psi. The alumina-to-charge ratio was approximately 2000/1. The eluate was monitored at 254 m$\mu$, and fractions were separated based upon the peaks observed in the ultraviolet profile. Fractions were identified containing predominantly leurosine, vinblastine, des-N-methylvinblastine and vincristine by thin layer chromatography. Concentration to dryness of the combined fractions containing vincristine yielded 18.7 mg of alkaloid. The residue was dissolved in 20 volumes of anhydrous ethanol, insolubles were separated by centrifugation and the pH of the supernate adjusted to 4.2 with 3 percent ethanolic sulfuric acid, thus forming vincristine sulfate. The crystallization mixture was allowed to stand at ambient temperature for two hours. The vincristine sulfate was then separated by centrifugation, and the centrifugate washed with ethanol and dried in vacuo. Weight of vincristine thus obtained was 12.3 mg (equivalent to 14.1 mg/kg of leaf extracted). The properties of vincristine sulfate thus obtained were identical to those recorded in the literature.

Alternatively, 10 g. of VRA were dissolved in 5 volumes of anhydrous ethanol. The pH of the solution was adjusted to 4.2 by the addition of 3 percent ethanolic sulfuric acid. The sulfate mixture was seeded to vinblastine sulfate. The crystallization mixture was allowed to stand for 48 hours and the dimeric alkaloid sulfate mixture was harvested by centrifugation. Processing as in the above procedure, following the gel exclusion chromatography step with chromatography over deactivated alumina at high pressure yielded 20.6 mg. of vincristine sulfate equivalent to 11.8 mg/kg of leaf extracted.

Vinblastine, leurosine, vinrosidine, des-N-methylvinblastine and the other dimeric alkaloids are obtained in similar fashion either as the free base or as the sulfate salt from eluate fractions rich in the particular alkaloid obtained during the high-pressure chromatography over deactivated alumina.

EXAMPLE 2

Vinblastine Purification

Fractions from the alumina high-pressure chromatography procedure of Example 1 identified as containing predominantly vinblastine were combined by thin-layer chromatography, and the combined fractions concentrated to dryness in vacuo. The resulting residual dimeric alkaloids consisting essentially of vinblastine and some residual leurosine were dissolved in a methanol-ethanol solvent mixture. Leurosine is insoluble in this mixture and precipitates. After separation of leurosine by centrifugation, the supernate containing vinblastine was decanted. The pH of the solution was adjusted to the range pH = 4–5 by the addition of ethanolic sulfuric acid, thus converting vinblastine and other alkaloids present to the corresponding sulfate salts. The sulfates were collected, the filtrate being discarded, and then the sulfates were reconverted to their respective free bases in the usual manner. Rechromatography of the free bases over alumina (activity III) at a 60:1 alumina-to-charge weight ratio using benzene-chloroform as the mobile phase, yielded fractions containing vinblastine (as identified by thin layer chromatography) and no other dimeric alkaloids. The vinblastine-containing fractions wer combined, and the solvent removed therefrom in vacuo. Recrystallization of the residual vinblastine from methanol yielded purified vinblastine which was in turn dissolved in ethanol and converted to the corresponding sulfate salt by treatment with ethanolic sulfuric acid. Vinblastine sulfate thus prepared was a single spot material by thin layer chromatography.

EXAMPLE 3

Des-N-methylvinblastine-Vincristine Conversion

Two hundred seventy kilograms of dry *Catharanthus roseus* leaves were processed according to the procedure of Example 1. Fractions identified as containing des-N-methyl-vinblastine by thin-layer chromatography were separated at the high pressure liquid chromatography step and concentrated under vacuum to dryness. Using the method described in Gorman, U.S. Pat. No. 3,354,163, 7.73 grams of crude des-N-methylvinblastine thus obtained were converted to vincristine at ambient temperature by addition to a solution containing 927 ml of 98% formic acid and 154 ml. of acetic anhydride. After the reaction was complete, as confirmed by thin-layer chromatography, the reaction mixture was concentrated under vacuum to a syrup. The concentrate was dissolved in 100 volumes of water, and the alkaloids converted to their free bases by extracting the aqueous solution at pH = 5.8 three times with methylenechloride. Concentration of the combined methylenechloride extracts under vacuum yielded 7.84 grams of vincristine free base. The free base was purified further by high pressure (200–300 p.s.i.) liquid chromatography in a 2.5 cm × 730 cm stainless steel column using 3200 g activity III-IV neutral alumina absorbent and ethyl acetate-methylenechloride-water (25:75:0.4) as mobile phase. Vincristine obtained after concentration to dryness of fractions identified as containing predominately vincristine amounted to 2.64 g. This material was crystallized twice from ethanol, rechromatographed using a methyl acetate-methylenechloride-water (48:52:1) mobile phase, crystallized in methanol and converted to sulfate in ethanol to yield 1.4 g vincristine sulfate (equivalent to 5.3 mg per kg of leaf extracted).

I claim:

1. A process for the purification of the dimeric vinca alkaloids — vincristine, des-N-methylvinblastine and vinblastine — which comprises the steps of extracting a plant source of said alkaloids with aqueous acid at a pH $\simeq$ 3, extracting the acidic solution thus obtained with a water-immiscible organic solvent, discarding the extract, adjusting the pH of the acidic solution to pH $\simeq$ 6 by the addition of alkali metal hydroxide or ammonium hydroxide, extracting the pH $\simeq$ 6 layer with a water-immiscible organic solvent, discarding the aqueous layer, separating and evaporating the solvent from the organic extract to obtain residual alkaloids, further purifying the residual alkaloids either (a) by subjecting them to gel exclusion chromatography in a pH = 7 aqueous buffer, extracting the dimeric indole alkaloids from aqueous buffer eluate fractions determined to contain them by standard analytical procedures with a water-immiscible organic solvent, separating the extracts, evaporating the extracting solvent therefrom, dissolving the partially purified residual alkaloids thus obtained in a lower alkanol, separating by centrifugation precipitated crystalline leurosine thus formed therefrom, adjusting the pH of the filtrate to pH $\simeq$ 4.2 by the addition of sulfuric acid, filtering the precipitated crystalline dimeric indole alkaloid sulfate salts thus formed, treating an aqueous solution of the isolated sulfates with alkali, thus forming the corresponding free bases, chromatographing the free bases over alumina at high pressure thereby separating vincristine, des-N-methylvinblastine and vinblastine from other alkaloids and from each other, collecting eluate fractions each consisting essentially of a separated alkaloid and crystallizing vincristine, des-N-methylvinblastine and vinblastine from said collected eluate fractions in purified form or (b) by dissolving them directly in a lower alkanol, separating precipitated crystalline leurosine thus formed therefrom, adjusting the pH of the filtrate to pH $\simeq$ 4.2 by the addition of sulfuric acid, filtering the precipitated crystalline dimeric indole alkaloid sulfate salts thus formed, treating an aqueous solution of the isolated sulfates with alkali, thus forming the corresponding free bases, chromatographing the free bases over alumina at high pressure thereby separating vincristine, des-N-mehtylvinblastine and vinblastine from other alkaloids and from each other, collecting eluate fractions each consisting essentially of a separated alkaloid and crystallizing vincristine, des-N-methylvinblastine and vinblastine from said collected eluate fractions in purified form.

2. A process for purifying the dimeric indole alkaloids, vincristine and vinblastine, in which the following essential steps are carried out in the order described:
   a. Extraction of vinca leaves with mineral acid at about pH ** 3;
   b. Making the extract basic by the addition of alkali, and extracting the dimeric alkaloids into an aromatic solvent;
   c. Conversion by addition of sulfuric acid of the dimeric alkaloids to sulfate salts;
   d. High-pressure alumina chromatography of the dimeric alkaloids as free bases or as sulfate salts;
   e. Collection of chromatographic fractions containing purified separated vincristine, des-N-methylvinblastine and vinblastine substantially free from other dimeric vinca alkaloids and from each other.

* * * * *

UNITED STATES PATENT AND TRADEMARK OFFICE
CERTIFICATE OF CORRECTION

PATENT NO. : 3,932,417
DATED : January 13, 1976
INVENTOR(S) : William E. Jones

It is certified that error appears in the above-identified patent and that said Letters Patent are hereby corrected as shown below:

Column 6, line 14, change "7" to --3--.
Column 6, line 54, change "**" to -- = --.

Signed and Sealed this

Fifth Day of October 1976

[SEAL]

Attest:

RUTH C. MASON
Attesting Officer

C. MARSHALL DANN
Commissioner of Patents and Trademarks